United States Patent [19]

Kawada et al.

[11] Patent Number: 5,169,643
[45] Date of Patent: Dec. 8, 1992

[54] THIOLCARBAMATE GRANULE FORMULATION

[75] Inventors: Hiroshi Kawada; Susumu Suzuki; Hiroki Tokunaga; Masaji Kikuta, all of Tokyo, Japan

[73] Assignee: Hodogaya Chemical Co., Ltd., Tokyo, Japan

[21] Appl. No.: 515,623

[22] Filed: Apr. 27, 1990

[30] Foreign Application Priority Data

May 10, 1989 [JP] Japan ................................ 1-115197

[51] Int. Cl.$^5$ .............................................. A61K 9/16
[52] U.S. Cl. .................................... 424/489; 71/64.13; 71/100; 71/DIG. 1; 558/232; 424/490; 424/491; 514/770
[58] Field of Search ........................ 424/489, 490, 491; 514/770; 558/232; 71/64.13, 100, DIG. 1

[56] References Cited

U.S. PATENT DOCUMENTS

| | | | |
|---|---|---|---|
| 3,940,484 | 2/1976 | Baker et al. | 424/248 |
| 4,132,780 | 1/1979 | McConnell | 424/127 |
| 4,207,089 | 6/1980 | Gay | 71/90 |
| 4,251,262 | 2/1981 | Brookes et al. | 71/92 |
| 4,582,528 | 4/1986 | Gray et al. | 71/100 |
| 4,788,217 | 11/1988 | Lányi et al. | 514/469 |

FOREIGN PATENT DOCUMENTS

2085301  9/1981  United Kingdom .

OTHER PUBLICATIONS

Chemical Abstract Reference #101:130592j (1984).
Chemical Abstract Reference #97:87072z (1982).
Chemical Abstract Reference #98:84881x (1983).
Chemical Patents Index, Basic Abstracts Journal, week J47, Jan. 26, 1983, section C, abstract No. 1436, Derwent Publications Ltd., London, GB; & JP-A-57-169-404 (Hodogaya Chem. Ind. K.K.) 10-0401981.
Chemical Patents Index, Basic Abstracts Journal, week K15, Jun. 8, 1983, section C, abstracts No. 35782, Derwent Publications Ltd. London, GB; & JP-A-58 038 204 (Hodogaya Chem. Ind. K.K.) Aug. 31, 1981.
Chemical Patents Index, Basic Abstracts Journal, week K20, Jul. 1983, section C, abstract No. 47909, Derwent Publications Ltd. London, GB; & JP-A-58 059 905 (Hodogaya Chem. Ind. K.K.) Jun. 10, 1981.
Chemical Patents Index, Basic Abstracts Journal, week E39, Nov. 24, 1982, section C, abstract No. 82116, Derwent Publications Ltd., London, GB; & JP-A-57 134 402 (Hodogaya Chem. Ind. K.K.) Dec. 2, 1981.
"The Merck Index", tenth edition, 1983, p. 4194, No. 4197, Merck & Co., Inc., Rahway, N.J., US.

Primary Examiner—Thurman K. Page
Assistant Examiner—Robert H. Harrison
Attorney, Agent, or Firm—Oblon, Spivak, McClelland, Maier & Neustadt

[57] ABSTRACT

A thiolcarbamate granule formulation comprising granules consisting essentially of Fuller's earth and a thiolcarbamate of the following formula I or II impregnated in the granules:

$$C_mH_{2m+1} \atop C_nH_{2n+1}} \!\!\!\!\!\! \diagup\!\!\!\!\!\text{N}-\text{C}(=\text{O})-\text{SC}_pH_{2p+1} \qquad (I)$$

wherein m is an integer of from 0 to 4, n is an integer of from 1 to 4, and p is an integer of from 1 to 5, provided that the sum of m+n+p is at most 7.

$$\text{(cyclohexyl)}-\text{N}-\text{C}(=\text{O})-\text{SCH}_3 \qquad (II)$$

7 Claims, No Drawings

THIOLCARBAMATE GRANULE FORMULATION

The present invention relates to a thiolcarbamate granule formulation for an agricultural or horticultural drug.

Today's agriculture secures high productivity by means of fertilizers, agricultural chemicals and various agricultural materials. Particularly, use of agricultural chemicals is indispensable for modern agriculture. On the other hand, the adverse effects of agricultural chemicals to the environment have been pointed out as serious problems. It is therefore important that agricultural chemicals provide adequate effects at low doses.

Thiolcarbamates used in the present invention are useful as nematocides, but they are susceptible to the influence of the temperature or the nature of soil, and at a high temperature or in sandy soil, they are likely to be dissipated in the atmosphere without adequately providing the nematocidal activities. Therefore, there has been a problem that they are obliged to be used at high concentrations of the active ingredients.

Under these circumstances, it is an object of the present invention to solve such a problem and to provide a thiolcarbamate formulation which is effective at a low dose.

The present invention provides a thiolcarbamate granule formulation comprising granules consisting essentially of Fuller's earth and a thiolcarbamate of the following formula I or II impregnated in the granules:

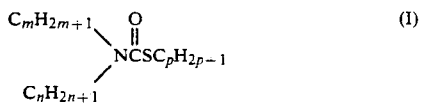
(I)

wherein m is an integer of from 0 to 4, n is an integer of from 1 to 4, and p is an integer of from 1 to 5, provided that the sum of $m+n+p$ is at most 7.

(II)

Now, the present invention will be described in detail with reference to the preferred embodiments.

The present inventors have impregnated thiolcarbamates to granules made of various minerals and have studied the retention times of the active ingredients. As a result, they have found that a remarkable extension of the retention time is observed when the thiolcarbamates are impregnated in granules made essentially of Fuller's earth or bleaching earth. The present invention has been accomplished on the basis of this discovery.

The thiolcarbamates useful for the present invention include those disclosed in Japanese Unexamined Patent Publications No. 70804/1982, No. 70805/1982, No. 134402/1982, No. 169404/1982, No. 38204/1983, No. 59905/1983 and No. 48407/1984.

The granules may be those obtained by pulverizing natural Fuller's earth or bleaching earth, followed by sieving, or they may be the ones obtained by kneading such pulverized Fuller's earth with water, followed by granulation by a usual granulation method. The granulated products are particularly preferred, since their strength is constant and they are free from dusting at the time of the application of the formulation. Further, Fuller's earth powder may be treated with a mineral acid, then washed with water and granulated.

Such Fuller's powder may be used alone. However, for the purpose of facilitating the granulation, other mineral powders may be incorporated, or for the purpose of improving the migration of the active ingredient to soil, a small amount of a surfactant may be added. Further, for the purpose of preventing the disintegration of the granules by water, a binding agent or a high boiling point oil or fat, may be added thereto.

However, the larger the content of Fuller's earth, the longer the retention time of the active ingredient can be extended.

There is no particular restriction as to the size of the granules. However, it is usually within a range of from 4 to 48 mesh, preferably from 12 to 24 mesh.

Likewise, there is no particular restriction as to the amount of the thiolcarbamate impregnated in the granules. However, the thiolcarbamate of the formula I or II is impregnated usually in an amount of from 0.5 to 20 parts by weight, preferably 1 to 15 parts by weight, more preferably 2 to 10 parts by weight, per 100 parts by weight of the granules.

Now, the present invention will be described in further detail with reference to Examples. However, it should be understood that the present invention is by no means restricted to such specific Examples.

EXAMPLE 1

10 Parts by weight of S-methyl N,N-dimethylthiolcarbamate (bp. 185° C.) (hereinafter referred to simply as MMTC), S-methyl N-methyl-N-ethylthiolcarbamate (bp. 198° C.) (hereinafter referred to simply as METC) or S-methyl N-methyl-N-propylthiolcarbamate (pb. 215° C.) (hereinafter referred to simply as MPTC) was impregnated to 90 parts by weight of Fuller's earth (produced in Yamagata-ken or Niigata-ken, Japan) pulverized and sieved to have a particle size of from 14 to 16 mesh. One g of the impregnated product was spread uniformly in a Petri dish having a diameter of 9 cm and left to stand at $23°\pm2°$ C. under air circulation of 3.5 m/min. The thiolcarbamate was extracted periodically with acetone and quantitatively analyzed by gas chromatography. For the purpose of comparison, experiments were conducted also with respect to other minerals (diatomaceous earth, Ca-bentonite, natural zeolite and pumice) in the same manner. The results are shown in Table 1.

Each experiment was repeated twice, and the average value of the content was divided by the initial value, whereupon the product was taken as the retention (%).

TABLE 1

| Carrier | Thiolcarbamate | Retention (%) | | |
|---|---|---|---|---|
| | | 1 day later | 5 days later | 9 days later |
| Fuller's earth | MMTC | 99 | 96 | 88 |
| (Produced in | METC | 97 | 92 | 87 |
| Yamagata-ken, | MPTC | 97 | 94 | 86 |
| Japan) | | | | |
| Fuller's earth | MMTC | 97 | 88 | 71 |
| (Produced in | METC | 96 | 81 | 66 |
| Niigata-ken, | MPTC | 94 | 80 | 67 |
| Japan) | | | | |
| Diatomaceous | MMTC | 0 | — | — |
| earth | METC | 0 | — | — |
| (Calcined | MPTC | 0 | — | — |
| product) | | | | |
| Ca-bentonite | MMTC | 77 | 49 | 34 |

TABLE 1-continued

| Carrier | Thiol-carbamate | Retention (%) | | |
|---|---|---|---|---|
| | | 1 day later | 5 days later | 9 days later |
| (Produced in Gunma-ken, Japan) | METC | 72 | 42 | 32 |
| | MPTC | 76 | 47 | 34 |
| Natural zeolite (Produced in Akita-ken, Japan) | MMTC | 16 | — | — |
| | METC | 18 | — | — |
| | MPTC | 30 | — | — |
| Pumice (Produced in Ishikawa-ken, Japan) | MMTC | 3 | — | — |
| | METC | 5 | — | — |
| | MPTC | 4 | — | — |

EXAMPLE 2

A powder of Fuller's earth (produced in Yamagata-ken, Japan) was kneaded with water and then extruded and granulated by a granulation machine with an outlet diameter of from 0.8 to 2.0 mm, followed by drying and pulverization. To 95 parts by weight of the pulverized product, 5 parts by weight of METC or MPTC was impregnated, and an experiment was conducted at a temperature of from 20° to 21° C. under air circulation of 3.5 m/min. In the same manner, Fuller's earth (produced in Yamagata-ken, Japan) was pulverized and sieved to have a particle size of from 14 to 16 mesh, and to 95 parts by weight of the sieved product, 5 parts of METC was impregnated. The experiment was conducted under the same conditions as above.

Further, for the purpose of comparison, experiments were conducted under the same conditions as above also with respect to those obtained by impregnating 5 parts by weight of METC to 95 parts by weight of A-type synthetic zeolite (8-12 mesh) having a pore size of 5 Å and X-type synthetic zeolite (8-12 mesh) having a pore size of 13 Å, respectively.

Each experiment was repeated twice, and the quantitative analysis and calculation were conducted in the same manner as in Example 1. The results are shown in Table 2.

TABLE 2

| Carrier | Thiol-carbamate | Retention (%) | | | |
|---|---|---|---|---|---|
| | | 1 day later | 5 days later | 8 days later | 15 days later |
| Fuller's earth (Outlet diameter: 2.0 mm) | METC | 96 | 96 | 94 | 93 |
| | MPTC | 102 | 99 | 99 | 96 |
| Fuller's earth (Outlet diameter: 1.2 mm) | METC | 97 | 96 | 97 | 94 |
| | MPTC | 97 | 98 | 98 | 96 |
| Fuller's earth (Outlet diameter: 0.8 mm) | METC | 101 | 101 | 101 | 100 |
| | MPTC | 97 | 97 | 97 | 97 |
| Fuller's earth (Pulverized product) | METC | 102 | 100 | 99 | 96 |
| A-type synthetic zeolite | METC | 21 | 4 | — | — |
| X-type synthetic zeolite | METC | 72 | 31 | 11 | — |

EXAMPLE 3

In the same manner as in Example 2, Fuller's earth (produced in Yamagata-ken, Japan) was kneaded with water and then extruded and granulated by a granulation machine with an outlet diameter of 1.0 mm, followed by drying and pulverization. To 90 parts by weight of the pulverized product, 10 parts of S-ethyl N-ethylthiolcarbamate (hereinafter referred to simply as SEETC), S-methyl N,N-diethylthiolcarbamate (hereinafter referred to simply as DETC) or S-propyl N,N-diethylthiolcarbamate (hereinafter referred to simply as SPDETC) was impregnated. The experiment was conducted at a temperature of from 20° to 21° C. under air circulation of 3.5 m/min.

For the purpose of comparison, experiment was conducted under the same condition as above with respect to the one obtained by impregnating 10 parts by weight of the same thiolcarbamate to 90 parts by weight of X-type synthetic zeolite (8-12 mesh) having a pore size of 13 Å.

Each experiment was repeated twice, and the quantitative analysis and calculation were conducted in the same manner as in Example 1. The results are shown in Table 3.

TABLE 3

| Carrier | Thiol-carbamate | Retention (%) | | |
|---|---|---|---|---|
| | | 1 day later | 3 days later | 7 days later |
| Fuller's earth (Outlet diameter: 1.0 mm) | SEETC | 98 | 101 | 99 |
| | DETC | 101 | 98 | 98 |
| | SPDETC | 98 | 99 | 100 |
| X-type synthetic zeolite | SEETC | 84 | 68 | 54 |
| | DETC | 78 | 53 | 39 |
| | SPDETC | 81 | 57 | 42 |

EXAMPLE 4

To a powder of Fuller's earth (produced in Yamagata-ken, Japan), other mineral powder, a surfactant, a binder, oil or fat, was added, and in the same manner as in Example 2, the mixture was kneaded with water and then extruded and granulated by a granulation machine with an outlet diameter of 1.2 mm, followed by drying and pulverization. To 85 parts by weight of the pulverized product, 15 parts by weight of MMTC was impregnated, and the experiment was conducted at a temperature of 25°±2° C. under air circulation of 3.5 m/min. Each experiment was repeated twice, and the quantitative analysis and calculation were conducted in the same manner as in Example 1. The retention after 24 hours was obtained. The results are shown in Table 4.

TABLE 4

| Carrier composition, wt. % in the bracket ( ) | | | | Retention |
|---|---|---|---|---|
| Fuller's earth (wt %) | Other mineral | Surfactant | Binder, oil or fat | (%) after 24 hours |
| 100 | — | — | — | 75 |
| 75 | Na-bentonite (25) | — | — | 66 |
| 50 | Na-bentonite (50) | — | — | 60 |
| 90 | — | — | Castor oil (10) | 43 |
| 90 | — | — | Corn oil (10) | 35 |

TABLE 4-continued

| Carrier composition, wt. % in the bracket ( ) | | | | Retention (%) after 24 hours |
|---|---|---|---|---|
| Fuller's earth (wt %) | Other mineral | Surfactant | Binder, oil or fat | |
| 98 | — | — | Sodium polyacrylate (2) | 69 |
| 98 | — | — | Polyvinyl alcohol (2) | 67 |
| 98 | — | Sodium alkylsulfosuccinate (2) | — | 61 |
| 98 | — | Polyoxyethylene nonylphenyl ether (2) | — | 62 |

EXAMPLE 5

Fuller's earth (produced in Yamagata-ken, Japan) pulverized and sieved to have a particle size of from 12 to 24 mesh. To the pulverized Fuller's earth, METC was impregnated to obtain a granule formulation having 5% or 10% of METC impregnated.

Each granule formulation was applied in an amount corresponding to 20 kg/10a to a field infested with meloidogyne incognita and mixed to the soil by a small size tiller. Then, five cucumber seedlings (Natsuaki No. 1) per unit section were planted. Cucumbers were harvested once a week. The amounts of cucumbers harvested four times during the period from one month after the plantation to two months after the plantation were totalled, and finally the average amount harvested per seedling per week was obtained.

Further, the parasitic degree of meloidogyne incognita upon expiration of two months after the plantation, was investigated. The parasitic degree of meloidogyne incognita was evaluated by the following standards.

| Parasitic degree of meloidogyne incognita | Damage to the roots (%) |
|---|---|
| 0 | 0 |
| 1 | 1–25 |
| 2 | 26–50 |
| 3 | 51–75 |
| 4 | 76–100 |

The experiment was repeated three times with an area of 3 m²/unit section, whereupon an average value was obtained.

For the purpose of comparison, METC was impregnated to natural zeolite (produced in Akita-ken, Japan) to obtain a granule formulation having 5% or 10% of METC impregnated. The experiment was conducted under the same condition as in the case of Fuller's earth (produced in Yamagata-ken, Japan). Further, the experiment was conducted also in a non-treated area.

The average amount of cucumbers per seedling per week and the parasitic degree of meloidogyne incognita, were obtained. The results are shown in Table 5.

TABLE 5

| Granule formulation | | Average amount harvested per week (g) | Parastic degree of Meloidogyne incognita |
|---|---|---|---|
| Mineral species | METC content | | |
| Fuller's earth | 5% | 593 | 1.20 ± 0.41 |
| Fuller's earth | 10% | 569 | 0.67 ± 0.49 |
| Zeolite | 5% | 487 | 2.07 ± 0.46 |
| Zeolite | 10% | 584 | 1.07 ± 0.70 |
| Non-treated unit section | | 241 | 3.40 ± 0.63 |

As described in the foregoing, the granule formulation having a thiolcarbamate impregnated in the granules of Fuller's earth has a retention time of the thiolcarbamate as the active ingredient remarkably prolonged as compared with the cases where other minerals are used as carriers, under open conditions. Also when the granule formulation of the present invention is used in a field, a significant increase in the nematocidal effects has been observed.

We claim:

1. A thiolcarbamate granule nematicidal formulation consisting essentially of Fuller's earth impregnated with 0.5 to 20 parts by weight per 100 parts by weight of the granules of S-methyl N,N-dimethyl-thiolcarbamate, S-methyl N-methyl-N-ethylthiolcarbamate, S-methyl N-methyl-N-propylthiolcarbamate, S-ethyl N-ethylthiolcarbamate, or S-propyl N,N-diethylthiolcarbamate.

2. The thiolcarbamate granule formulation according to claim 1, wherein the thiolcarbamate is S-methyl N,N-dimethylthiolcarbamate.

3. The thiolcarbamate granule formulation according to claim 1, wherein the thiolcarbamate is S-methyl N-methyl-N-ethylthiolcarbamate.

4. The thiolcarbamate granule formulation according to claim 1, wherein the thiolcarbamate is S-methyl N-methyl-N-propylthiolcarbamate.

5. The thiolcarbamate granule formulation according to claim 1, wherein the thiolcarbamate is S-ethyl N-ethylthiolcarbamate.

6. The thiolcarbamate granule formulation according to claim 1, wherein the thiolcarbamate is S-propyl N,N-diethylthiolcarbamate.

7. The thiolcarbamate granule formulation according to claim 1, wherein the granules have a size of from 12 to 24 mesh.

* * * * *